United States Patent [19]

Shikhman

[11] Patent Number: 5,776,156
[45] Date of Patent: Jul. 7, 1998

[54] ENDOSCOPIC CUTTING INSTRUMENT

[75] Inventor: Oleg Shikhman, Fairfield, Conn.

[73] Assignee: United States Surgical Corporation, Norwalk, Conn.

[21] Appl. No.: 488,845

[22] Filed: Sep. 5, 1995

[51] Int. Cl.⁶ .................................. A61B 17/32
[52] U.S. Cl. .................. 606/170; 606/167; 606/181; 606/182; 606/188
[58] Field of Search .................. 606/167, 170, 606/172, 171, 181, 182, 188

[56] References Cited

U.S. PATENT DOCUMENTS

| | | |
|---|---|---|
| 4,210,146 | 7/1980 | Banko . |
| 4,414,974 | 11/1983 | Dotson et al. . |
| 4,444,184 | 4/1984 | Oretorp . |
| 4,491,132 | 1/1985 | Aikins . |
| 4,499,898 | 2/1985 | Knepshield et al. . |
| 4,516,575 | 5/1985 | Gerhard et al. . |
| 4,576,164 | 3/1986 | Richeson . |
| 4,674,500 | 6/1987 | DeSatnick . |
| 4,730,613 | 3/1988 | Gordy . |
| 4,733,662 | 3/1988 | DeSatnick et al. . |
| 4,735,202 | 4/1988 | Williams . |
| 4,976,269 | 12/1990 | Mehl ............................ 606/170 |
| 4,991,600 | 2/1991 | Taylor .......................... 606/171 |
| 5,071,426 | 12/1991 | Dolgin et al. . |
| 5,116,351 | 5/1992 | Frassetti . |
| 5,139,507 | 8/1992 | Dolgin et al. . |
| 5,141,517 | 8/1992 | Shutt . |
| 5,176,695 | 1/1993 | Dulebohn ..................... 606/170 |
| 5,184,625 | 2/1993 | Cottone, Jr. et al. ......... 606/171 |
| 5,207,696 | 5/1993 | Matwijcow . |
| 5,211,652 | 5/1993 | Derbyshire . |
| 5,254,128 | 10/1993 | Mesa . |
| 5,258,001 | 11/1993 | Corman . |
| 5,273,519 | 12/1993 | Koros et al. ................. 606/171 |
| 5,275,606 | 1/1994 | Abidin et al. . |
| 5,292,329 | 3/1994 | Werner . |
| 5,292,330 | 3/1994 | Shutt . |
| 5,342,379 | 8/1994 | Volinsky . |
| 5,344,424 | 9/1994 | Roberts et al. . |
| 5,379,520 | 1/1995 | Collins . |
| 5,403,337 | 4/1995 | Platts . |
| 5,431,675 | 7/1995 | Nicholas et al. ............. 606/170 |

Primary Examiner—Michael Buiz
Assistant Examiner—Daphna Shaz

[57] ABSTRACT

An endoscopic cutting instrument to be used in conjunction with endoscopic surgical procedures, includes a housing member elongated tubular member connected to the housing member and extending distally therefrom, a drive member at least partially accommodated within the tubular member and reciprocally longitudinally movable therein, a blade member disposed at a distal end of the drive member and defining a cutting edge for incising tissue and an actuating member associated with the housing member and operatively connected to the drive member. The actuating member is movable to cause corresponding movement of the drive member to at least partially expose the blade member beyond a distal end of the tubular member. The instrument also includes a release member associated with the actuating member. The release member is preferably movable between an engaged position preventing movement of the actuating member and a disengaged position permitting movement of the actuating member and corresponding movement of the drive member to at least partially expose the blade member. The instrument may also include a spring mechanism which automatically retracts the blade member upon release of the actuating member.

14 Claims, 4 Drawing Sheets

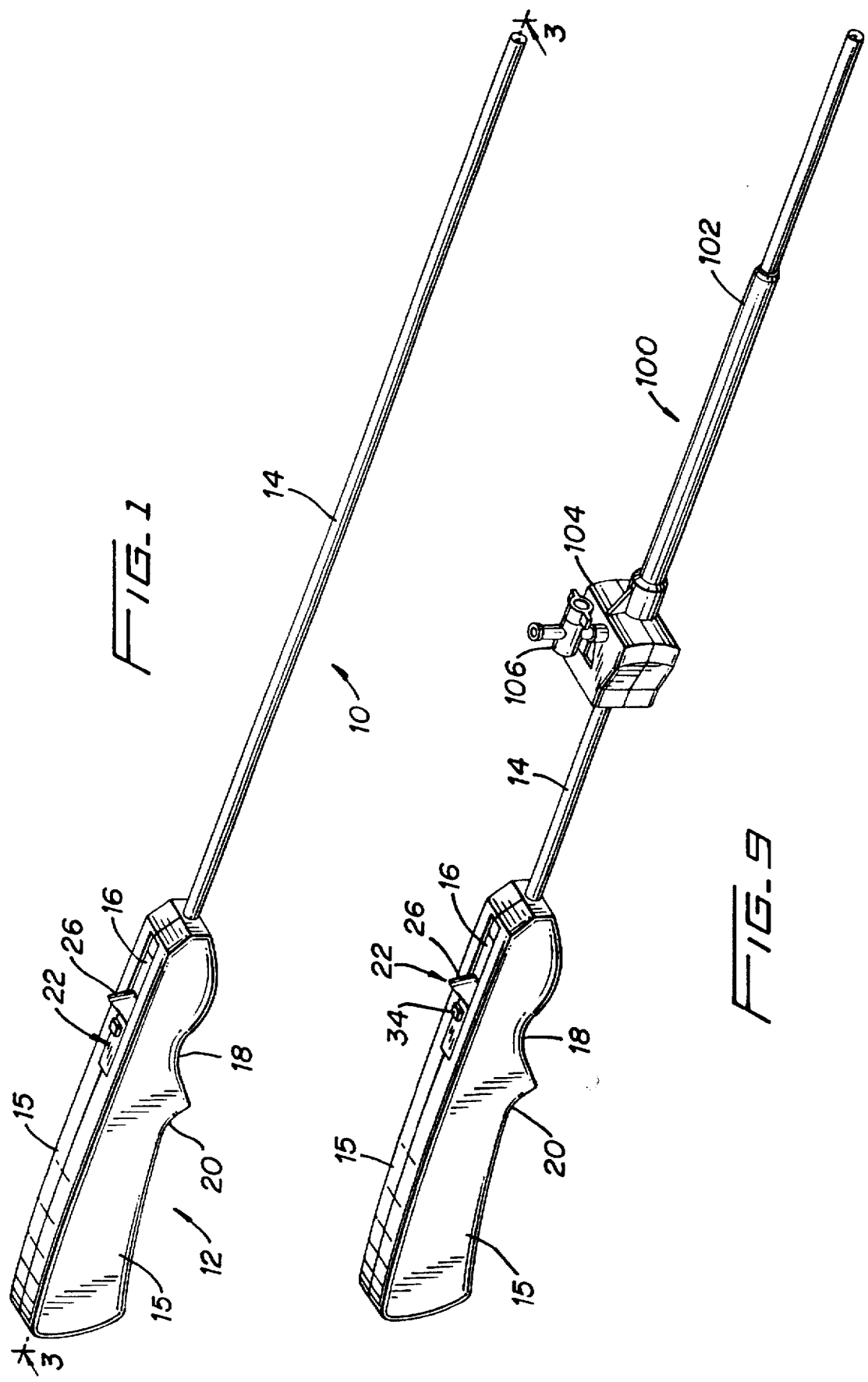

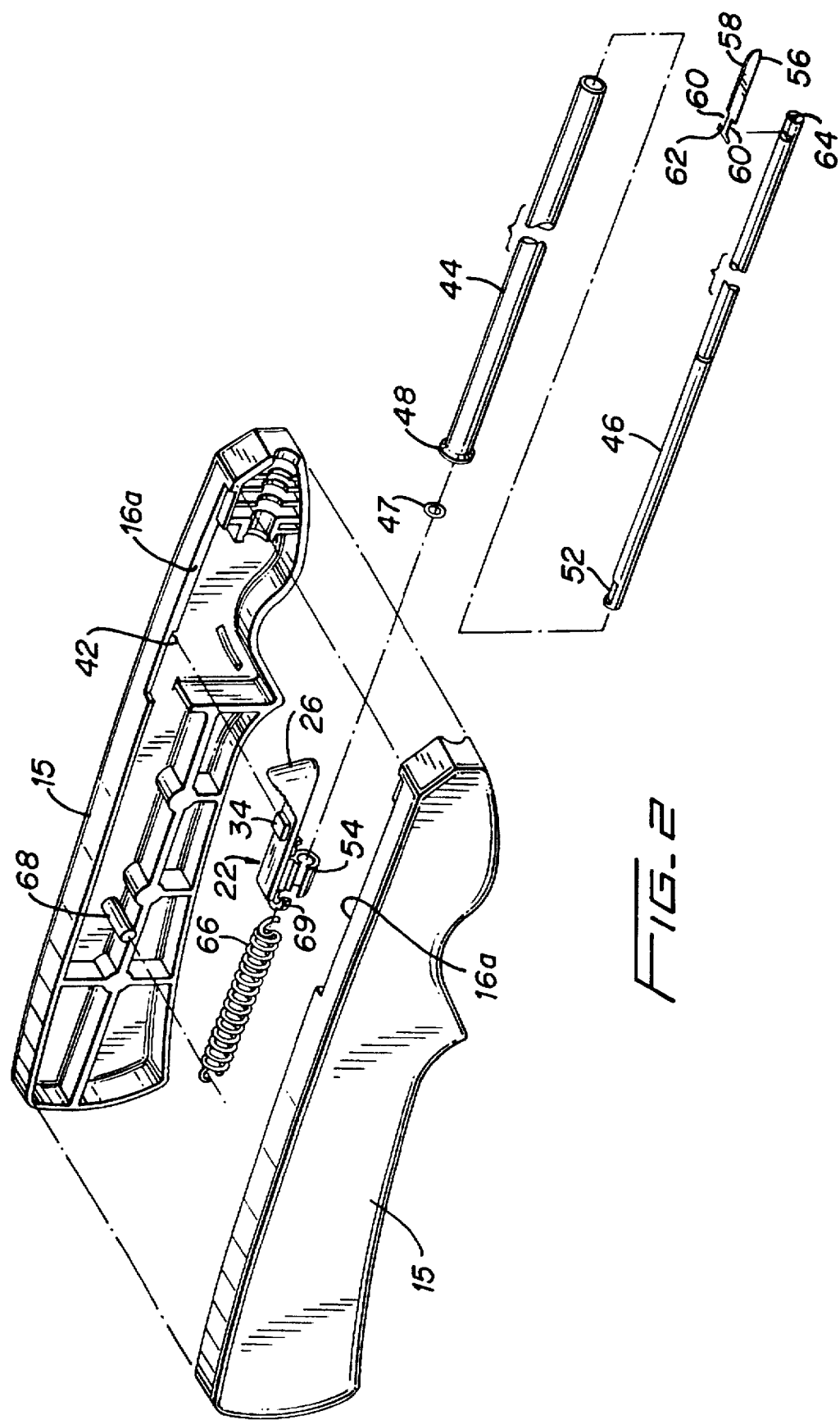

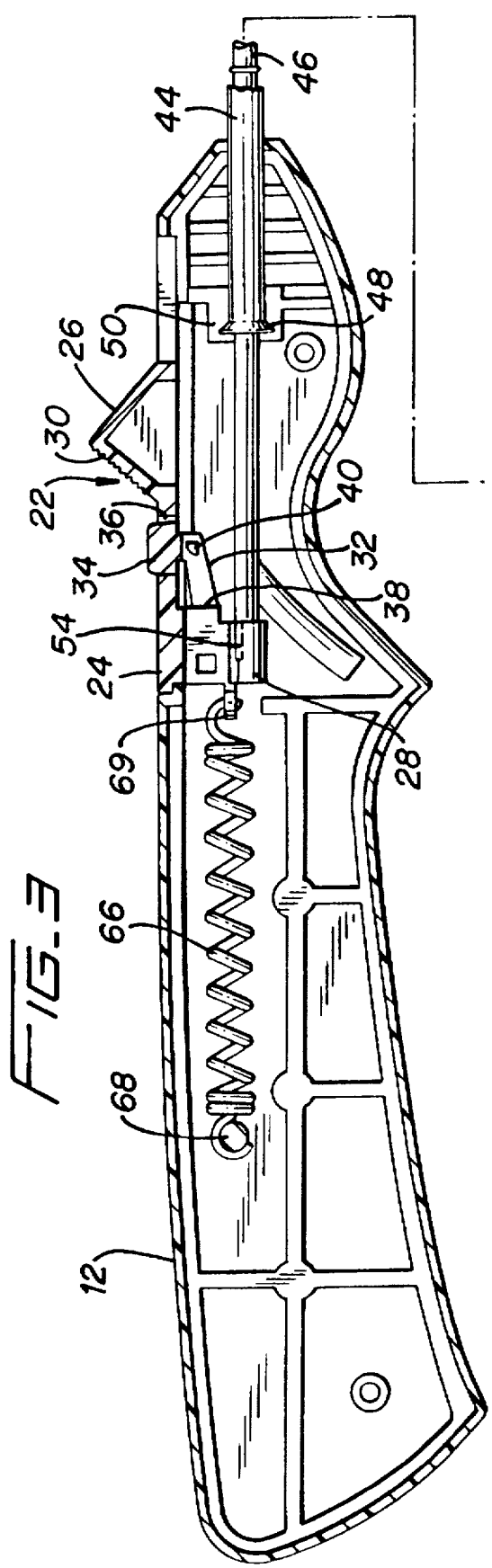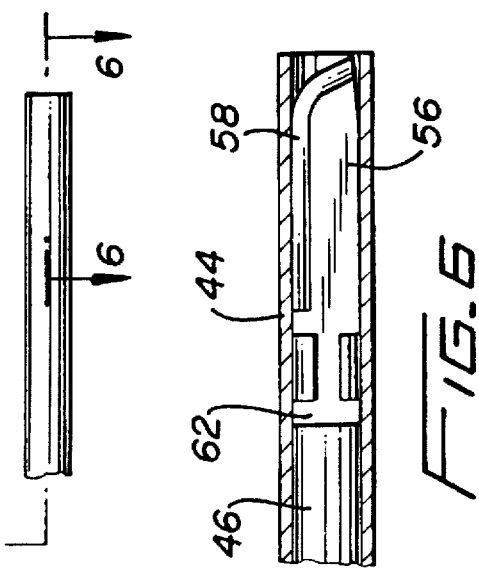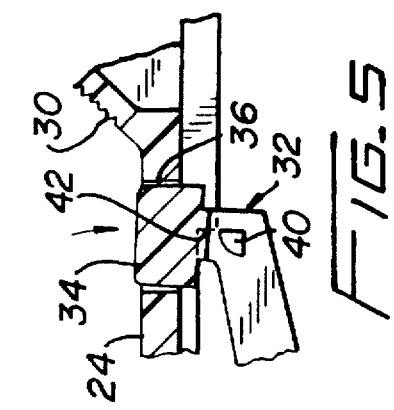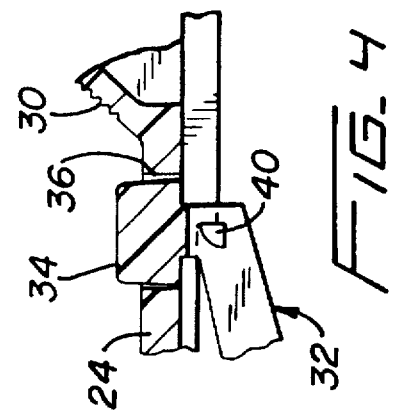

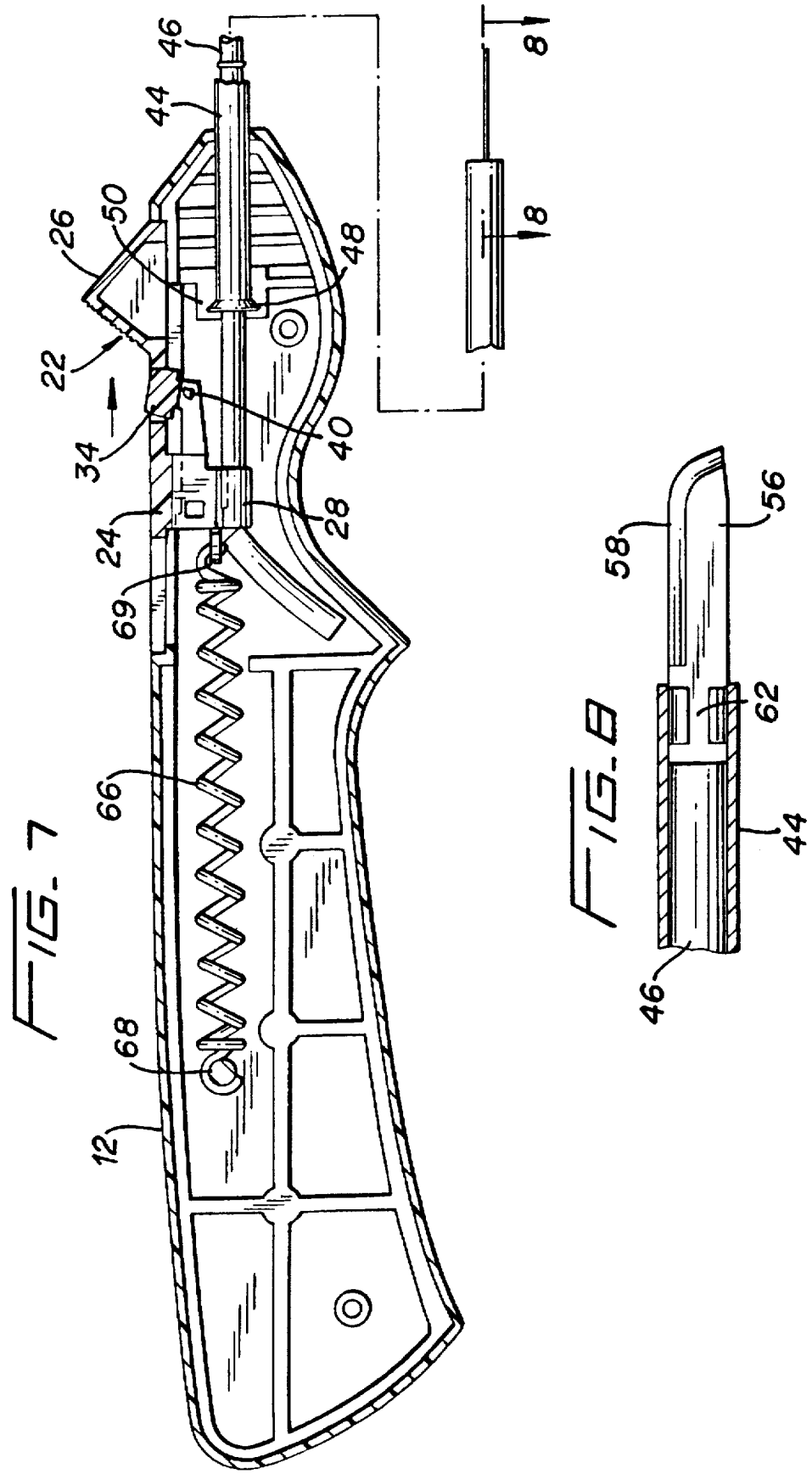

ENDOSCOPIC CUTTING INSTRUMENT

BACKGROUND

1. Field of the Disclosure

The present disclosure generally relates to surgical cutting instruments and, in particular, to a surgical scalpel useful in conjunction with endoscopic and laparoscopic surgical procedures.

2. Description of the Related Art

In endoscopic procedures, surgery is performed in any hollow viscus of the body through a small incision or through narrow endoscopic tubes (cannulas) inserted through small entrance wounds in the skin. In laparoscopic procedures, surgery is performed in the interior of the abdomen. Endoscopic and laparoscopic procedures often require the surgeon to operate on organs, tissue and vessels far removed from the incision, thereby requiring that any instruments used in such procedures be of sufficient size and length to permit remote operation.

The surgical environment of laparoscopic and endoscopic surgical procedures necessitates the undertaking of extreme care in manipulating a surgical instrument about the operative site as well as during the introduction and withdrawal of the instrument through the endoscopic portal. This is particularly true with cutting instruments having a cutting blade or edge at a remote end. The exposed cutting blade increases the potential for undesired incising of underlying tissue, viscera and organs within an operative site.

Surgical cutting instruments incorporating mechanisms to facilitate the atraumatic introduction and manipulation of the instrument about an operative site are known in the art. For example, U.S. Pat. No. 4,735,202 to Williams relates to a microsurgical knife having a blade guard in the form of a cylindrical sleeve while slides relative to a knife blade in position to cover the blade. A longitudinal slot and locking tab arrangement secures the blade guard in such blade covering position U.S. Pat. No. 4,576,164 to Richeson teaches an instrument wherein a shroud is moveable on a knife body to at least three positions, i.e., a rearward position fully exposing the blade, an intermediate position partially exposing the blade and a forward position covering the blade. The shroud can be locked in each of these positions by a groove and locking tab arrangement.

The instruments disclosed in the Williams '202 patent and the Richeson '164 patent are extremely limited in their uses. In particular, these instruments are not adaptable for endoscopic or laparoscopic surgical procedures. Secondly, exposing the cutting blade from the blade guard or shroud of these instruments requires a two handed procedure, i.e., one hand to steady the knife body and the other hand to manipulate the blade guard.

A further disadvantage with these known instruments is that the cutting blade remains exposed unless the operator actively moves the blade guard to the blade covering position. Thus, the potential for undesired incising of tissue is increased during the period prior to covering the blade.

Accordingly, the present disclosure is directed to a surgical cutting instrument having application in endoscopic and laparoscopic surgical procedures. The instrument incorporates structure which performs protective functions during application of the instrument and manipulation of the instrument about the surgical site.

SUMMARY

An endoscopic cutting instrument to be used in conjunction with endoscopic surgical procedures, includes a housing member dimensioned to be grasped by the hand of a user, an elongated tubular member connected to the housing member and extending distally therefrom, a drive member at least partially accommodated within the a longitudinal bore of the tubular member and reciprocally longitudinally movable therein, a blade member disposed at a distal end of the drive member and defining a cutting edge for incising tissue and an actuating member associated with the housing member and operatively connected to the drive member. The actuating member is movable to cause corresponding movement of the drive member to at least partially expose the blade member beyond a distal end of the tubular member. The instrument also includes a release member associated with the actuating member and engageable with the housing. The release member is preferably movable between an engaged position preventing movement of the actuating member and a disengaged position permitting movement of the actuating member and corresponding movement of the drive member to at least partially expose the blade member beyond the distal end of the tubular member. In one preferred embodiment, the release member is integrally connected to the actuating member about an integral hinge joint and movable about the hinge joint between the engaged and disengaged positions thereof. The instrument may also include a spring mechanism which automatically retracts the blade member upon release of the actuating member.

BRIEF DESCRIPTION OF THE PREFERRED DRAWING(S)

Preferred embodiment(s) of the disclosure are described hereinbelow with reference to the drawings wherein:

FIG. 1 is a perspective view of the endoscopic cutting instrument;

FIG. 2 is a perspective view with parts separated of the cutting instrument illustrating the components of the handle portion and the endoscopic portion;

FIG. 3 is a side plan view of the cutting instrument with the handle in cross-section illustrating the actuating member of the handle in a normal retracted position;

FIG. 4 is an enlarged sectional view illustrating the release member in an engaged position with a locking surface of the handle to prevent distal movement of the actuating member;

FIG. 5 is an enlarged sectional view similar to the view of FIG. 4 illustrating the release member depressed to cause disengagement from the locking surface to permit distal movement of the actuating member and deployment of the blade member;

FIG. 6 is a cross-sectional view of the distal end portion of the endoscopic portion taken along the lines 6—6 of FIG. 3 illustrating the blade member of the instrument in a retracted position contained within the endoscopic portion;

FIG. 7 is a view similar to the view of FIG. 3 illustrating the actuating member advanced to extend the blade member from the distal end portion of the endoscopic portion;

FIG. 8 is a cross-sectional view of the distal end portion of the endoscopic portion taken along the lines 8—8 of FIG. 7 illustrating the blade member in an advanced position extending beyond the endoscopic portion; and FIG. 9 is a perspective view of the endoscopic instrument of FIG. 1 used in conjunction with a cannula assembly during a laparoscopic surgical procedure.

DETAILED DESCRIPTION OF THE PREFERRED EMBODIMENT(S)

Referring now to FIG. 1, there is illustrated in perspective view the endoscopic cutting instrument in accordance with the principles of the present disclosure. Instrument 10 is intended to be used in conjunction with an endoscopic surgical procedure, i.e., surgery performed in any hollow viscus of the body through a small incision or through a cannula.

Referring now to FIG. 2, in conjunction with FIG. 1, instrument 10 includes housing or frame 12 and an endoscopic or tubular portion 14 extending distally from the frame 12. Frame 12 consists of two half sections 15 connected to each other along their peripheries by conventional means such as screws, fasteners, adhesives or the like. Half sections 15 are preferably fabricated from a suitable polymeric material such as a polycarbonate or a polystyrene, however, if intended as a re-usable instrument, it is envisioned that half sections 15 may be formed of stainless steel as well. Each half section 15 includes a generally longitudinal extending slot portion 16a in its upper surface. In the assembled condition of half sections 15, slot portions 16a define an enclosed longitudinal slot 16 (FIG. 1). Frame 12 further includes contoured surfaces 18, 20 which are each dimensioned for grasping by the user to facilitate manipulation of the instrument 10 about the operative site.

Referring now to FIGS. 2–3, instrument 10 further includes an actuating member, identified generally by reference numeral 22. Actuating member 22 is at least partially accommodated within longitudinal slot 16 of frame 12 and is movable relative to the frame between an unadvanced (retracted) position and an advanced position as will be discussed. As shown in FIGS. 3 and 4, actuating member 22 includes a base portion 24 and a generally triangular-shaped projecting portion 26 extending from the base portion 24 through longitudinal slot 16 and beyond the upper surface of frame 12. Base portion 24 has a generally C-shaped lower mounting portion 28, the importance of which will be discussed hereinbelow. Projecting portion 26 is strategically dimensioned and oriented to be engaged by the thumb of the user and may include a serrated outer surface 30 to facilitate contacting engagement therewith.

Actuating member 22 further includes a release member 32 having a release button 34 which extends through an aperture 36 defined in base portion 24. Release member 32 is connected to the lower portion of base portion 24 by integral hinge joint 38 and is movable about the hinge joint 38 in a general vertical direction relative to frame 12 between upward and downward positions shown in FIGS. 4 and 5, respectively.

Referring now to FIGS. 4 and 5, in conjunction with FIG. 3, release member 32 includes a locking nub 40 extending from each of its sides. Locking nub 40 engages a vertical locking shelf 42 defined in frame 12 (FIGS. 2 and 5) when the release member 32 is in its normal upward position of FIGS. 3 and 4. In the downward or release position of release member 32 shown in FIG. 5, locking nub 40 is displaced downwardly to disengage from shelf 42 thus permitting distal longitudinal movement of the actuating member 22 as will be discussed below.

Actuating member 22 and release member 32 are preferably monolithically formed as a single unit from a resilient polymeric material such as polycarbonate or the like. Release member 32 is capable of flexing downwardly about hinge joint or living hinge 38 to its downward release position in response to a depressive force applied to release button 34 (i.e., in the direction of the directional arrow shown in FIG. 4) and returns to its upward or engaged position, in the absence of the depressive force, under the influence of the inherent resilient characteristics of its material of fabrication. Although shown as monolithically formed, it is also contemplated that the release member 32 can be a separate component.

Referring now to FIGS. 2–3, endoscopic portion 14 of instrument 10 will be described. Endoscopic portion 14 includes elongated tubular member 44 and drive or rod member 46 disposed within the longitudinal bore of the tubular member. Tubular member 44 has a proximal flanged portion 48 which is accommodated within a correspondingly dimensioned inner groove 50 defined within frame 12 to secure the tubular member 44 to the frame 12. Other conventional means for securing tubular member 44 to frame 12 are envisioned such as with use of adhesives, fasteners, etc.

The proximal end portion of rod member 46 is accommodated within C-shaped lower mounting portion 28 of actuating member 22 to mount the rod member 46 to the actuating member 22. In a preferred embodiment, the proximal end portion of rod member 46 includes a partial longitudinal slot 52 which receives a correspondingly dimensioned and configured partial longitudinal rib 54 (shown in phantom in FIG. 3; see also FIG. 2) extending form an inner surface of C-shaped mounting portion 28 to operatively connect these two components. In this manner, longitudinal movement of actuating member 22 translates into corresponding longitudinal movement of rod member 46. O-ring seal 47 is positioned on rod member 46 to prevent the egress of gases from the body if the surgery is performed in an insufflated body cavity.

A blade member 56 is connected to the distal end of rod member 46. Blade member 56 is generally of flat or planar construction having a single cutting edge 58 (FIG. 6) for incising tissue. The proximal portion of blade member 56 has opposed recessed portions 60 which define T-shaped mounting head 62. Mounting head 62 is received within correspondingly dimensioned T-shaped mounting groove 64 within rod member 46 to secure the blade member 56 to the rod member 44. Other means for securing blade member 56 to rod member 44 may be utilized by one skilled in the art such as with the use of screws, fasteners, adhesives, etc.

Referring still to FIGS. 2–3, a coiled spring 66 is connected at one end to frame 12 via mounting pin 68 and at its other end to actuating member 22 via connector portion 69. Spring 66 normally biases actuating member 22 and rod member 46 proximally to an unadvanced or proximalmost position. In the proximalmost position of actuating member 22, blade member 56 is wholly contained within tubular member 44 as shown in FIGS. 3 and 6.

Referring now to FIGS. 7–8, the operation of instrument 10 will be discussed. To expose blade member 56, release button 34 of release member 32 is depressed downwardly with the thumb of the user to cause downward movement of release member 32 and release of locking nubs 40 with frame 12 in a manner described above and as depicted in FIG. 5. With the release member 32 disengaged, actuating member 22 is capable of advancing movement (in the direction of the directional arrow shown in FIG. 7) to cause corresponding advancing movement of rod member 46 and deployment of blade member 56 to incise tissue.

Once the incising process is completed, actuating member 22 is released by the user which causes the actuating member 22, rod member 46 and blade member 56 to retract or move proximally to the position illustrated in FIG. 3 under the influence of coiled spring 66. It is to be appreciated that during proximal movement of actuating member 22, locking nubs 40 of release member 32 cam or flex downwardly to clear locking shelf 50 to assume its engaged position of FIGS. 3 and 4.

Thus, the instrument 10 of the present disclosure incorporates safety provisions 1) which prevent inadvertent advancement of the cutting blade 56 (i.e., in the form of release button 34 which must be depressed to advance actuating member 22) and 2) which cause automatic retraction of the cutting blade 56 upon release of actuating member 22. A further advantage of the instrument 10 is that only a one-handed operation is required to release the release member 32 and advance actuating member 22. Moreover, actuating member 22 and release button 34 of release member 32 are strategically dimensioned and positioned such that the user's thumb can simultaneously engage both components to release and advance the actuating member 22 so as to effectuate the advancement of cutting blade 56 without requiring any repositioning of th e hand on handle 12.

Referring now to FIGS. 1 and 9, instrument 10 may be used with a cannula during an endoscopic surgical procedure. Cannula 100 is a component of a trocar assembly which also consists of an obturator having a sharp pointed tip. The obturator is positionable within the cannula and the whole assembly is advanced into the body during an endoscopic procedure to gain access to the body tissue to be incised. The obturator is subsequently withdrawn from the cannula to permit the introduction of surgical instruments therethrough.

Cannula 100 includes a cannula sleeve 102 and a cannula housing 104 mounted on one end of the sleeve. Sleeve 102 defines a cannula passage in its interior and may be formed of a stainless steel or a rigid polymeric material. Cannula housing 104 is secured to the proximal end of sleeve 102 and defines a longitudinal opening for reception and passage of an elongated surgical instrument. A cannula seal (not shown) may be positioned within the interior of cannula housing 104 to form a fluid tight seal about an instrument inserted therein. A preferred seal is fabricated from a resilient material is capable of closing in the absence of an instrument so as to isolate the insufflated cavity from the ambient surroundings. A stop cock valve 106 may be incorporated as part of cannula housing 104 to permit the passage of insufflation gases through the cannula sleeve 102 and into the body cavity. A cannula assembly suitable for use with endoscopic instrument 10 is disclosed in commonly assigned U.S. Pat. No. 4,601,710 to Moll, the contents of which are incorporated herein by reference.

In use of instrument 10 with cannula 100 during an endoscopic procedure, the cannula 100 is positioned within the insufflated peritoneal cavity as described above. Thereafter, cutting instrument 10 with blade member 66 in its retracted position is positioned within the passageway defined by the cannula 100 and advanced to the desired location. Release button 34 of release member 32 is depressed and the actuating member 22 is advanced to expose cutting blade 56 beyond the distal end of tubular member 44 in the manner described above. The instrument can be used in a variety of surgical procedures. One application would be to excise a disc during an endoscopic discectomy procedure. Upon completion of the incising process, actuating member 22 is released to cause automatic retraction of blade member 56 within tubular member 44. The instrument 10 is subsequently withdrawn from the cannula 10 to permit the introduction of other surgical instrumentation, necessary to complete the procedure.

While the above description contains many specifics, these specifics should not be construed as limitations on the scope of the invention, but, merely as an exemplification of a preferred embodiment thereof. Those skilled in the art will envision other possible variations that are within the scope and spirit of the invention as defined by the claims appended hereto.

What is claimed is:

1. An endoscopic cutting instrument to be used in conjunction with endoscopic surgical procedures, which comprises:

a) a housing member dimensioned to be grasped by the hand of a user;

b) an elongated tubular member connected to the housing member and extending distally therefrom, the elongated member defining a longitudinal axis and having a longitudinal bore extending therethrough;

c) a drive member at least partially accommodated within the longitudinal bore of the tubular member and reciprocally longitudinally movable therein;

d) a blade member disposed at a distal end of the drive member and defining a cutting edge for incising tissue;

e) an actuating member associated with the housing member and operatively connected to the drive member, the actuating member movable to cause corresponding distal movement of the drive member to at least partially expose the blade member beyond a distal end of the tubular member; and f) a release member including a locking surface selectively engageable with one of the drive member and the housing member wherein engagement of the locking surface of the release member with one of the drive member and the housing member prevents distal movement of the drive member and exposure of the blade member beyond the distal end of the tubular member, the release member movable independent of movement of the actuating member to cause release of the locking surface from the one of the drive member and the housing member to permit distal movement of the drive member and exposure of the blade member.

2. The endoscopic cutting instrument according to claim 1 wherein the release member is associated with the actuating member, the release member movable between an engaged position and a disengaged position, wherein in the engaged position the release member prevents movement of the actuating member and wherein in the disengaged position the release member permits movement of the actuating member and corresponding movement of the drive member to at least partially expose the blade member beyond the distal end of the tubular member.

3. The endoscopic cutting instrument according to claim 2 wherein the locking surface of the release member is engageable with a locking shelf of the housing member when in the engaged position of the release member to prevent distal movement of the actuating member.

4. The endoscopic cutting instrument according to claim 3 wherein the release member is connected to the actuating member.

5. The endoscopic cutting instrument according to claim 4 wherein the release member is connected to the actuating member by an integral hinge joint, the release member movable about the hinge joint to disengage the locking surface from the locking shelf.

6. The endoscopic cutting instrument according to claim 5 wherein the actuating member and the release member are monolithically formed from a resilient polymeric material.

7. The endoscopic cutting instrument according to claim 1 wherein the actuating member is movable between first and second positions thereof, the first position of the retracting member corresponding to an unadvanced position of the drive member wherein the blade member is contained within the distal end of the tubular member, the second position of the actuating member corresponding to an advanced position of the drive member wherein the blade member is at least partially exposed beyond the distal end of the tubular member.

8. The endoscopic cutting instrument according to claim 7 including a spring member connected to the actuating member to normally bias the actuating member to the first position thereof.

9. The endoscopic cutting instrument according to claim 1 wherein the actuating member is longitudinally movable between the first and second positions thereof.

10. An endoscopic cutting instrument to be used in conjunction with endoscopic surgery, which comprises:

a) a frame; and
  b) an endoscopic portion connected to the frame and extending distally therefrom, the endoscopic portion including:
    i) an elongated tubular member defining a longitudinal axis;
    ii) a rod member at least partially disposed within the tubular member and reciprocally longitudinally movable therein between a proximalmost position and a distalmost position; and
    iii) a blade member connected to the rod member;
  c) an actuating member operatively connected to the rod member, the actuating member movable between first and second positions thereof, the first position corresponding to the proximalmost position of the rod member wherein the blade member is fully contained within the tubular member, the second position corresponding to the distalmost position of the rod member wherein the blade member is at least partially exposed beyond the tubular member;
  d) a spring member operatively connected to the actuating member for biasing the actuating member to the first position thereof; and
  e) a manually engageable release member operatively connected to the actuating member, the release member defining an engaging surface engageable with the frame to prevent movement of the actuating member to the second position thereof, wherein movement of the release member causes disengagement of the engaging surface with the frame to permit movement of the actuating member to the second position thereof, and wherein movement of the release member is independent of movement of the actuating member.

11. The endoscopic cutting instrument according to claim 10 wherein the release member is mounted to the actuating member.

12. The endoscopic cutting instrument according to claim 11 wherein the release member is at partially accommodated within a corresponding aperture defined in the actuating member.

13. The endoscopic cutting instrument according to claim 12 wherein the release member is connected to the actuating member by an integral hinge joint, the release member movable about the hinge joint such that the engaging surface is disengaged from the frame.

14. The endoscopic cutting instrument according to claim 9 wherein the actuating member is longitudinally movable between the first and second positions thereof.

* * * * *